United States Patent [19]

Kiser et al.

[11] 4,076,754

[45] Feb. 28, 1978

[54] FORMALDEHYDE MANUFACTURING PROCESS

[75] Inventors: Gary L. Kiser, Seabrook; Bobby G. Hendricks, Deer Park, both of Tex.

[73] Assignee: E. I. Du Pont de Nemours and Company, Wilmington, Del.

[21] Appl. No.: 650,801

[22] Filed: Jan. 20, 1976

[51] Int. Cl.$^2$ ............................................. C07C 45/16
[52] U.S. Cl. ................................. 260/603 C; 260/606
[58] Field of Search ............... 260/603 C, 606, 603 H, 260/603 R

[56] References Cited

U.S. PATENT DOCUMENTS

| | | | |
|---|---|---|---|
| 2,462,413 | 2/1949 | Meath | 260/606 |
| 3,928,461 | 12/1975 | Diem | 260/603 HF |

Primary Examiner—Bernard Helfin
Assistant Examiner—W. B. Lone

[57] ABSTRACT

In a process for the manufacture of formaldehyde by the silver-catalyzed oxidation of methanol in two stages, a composite catalyst is used in the second oxidation stage, which is prepared by sintering an upstream layer of foraminous silver having a void volume of 75 to 90% contiguous to a downstream layer of crystalline silver particles having a void volume of 65 to 75% which is at least about 5% below the void volume of the upper layer.

9 Claims, No Drawings

FORMALDEHYDE MANUFACTURING PROCESS

FIELD OF THE INVENTION

The invention relates to an improved process for the manufacture of formaldehyde by the oxidation of methanol. In particular, the invention relates to such a process in which the oxidation is carried out in the presence of a sintered silver catalyst.

BACKGROUND OF THE INVENTION

The reaction by which formaldehyde is obtained from methanol by catalytic oxidation has been known since 1868 and the use of silver catalysts for this purpose has been known at least since 1908 as is disclosed in German Pat. No. 228,687. Though other catalytic metals and metal oxides have been proposed and used, the use of silver for this process is quite widespread.

The basic method for carrying out the reaction comprises oxidizing an air-methanol mixture over silver catalyst and then recovering the formaldehyde by condensation and absorption with water. It is usually neccessary that the methanol content of the product be no greater than about 2% by weight in a 56% by weight aqueous solution of formaldehyde.

Silver-catalyzed processes for making formaldehyde from methanol can be characterized according to the number of catalytic stages used to effect the conversion. Single stage operation is quite widely used but suffers from the disadvantage that rather high amounts of unconverted methanol are contained in the product emerging from the catalyst bed. This phenomenon is customarily referred to as "methanol leakage". Since for many applications methanol is an undesirable contaminant, it must be separated from the formaldehyde solution. This entails a substantial investment is distillation facilities and energy to carry out such separations.

One way of reducing the need for facilities to distill off methanol is to use two oxidation stages with interstage cooling. A basic two-stage process of this type was disclosed in U.S. Pat. No. 2,462,413 to Meath. In Northeimer's allowed U.S. Pat. application Ser. No. 448,994, filed Mar. 7, 1974, an improvement on the Meath process is disclosed by which even lower amounts of methanol in the absorber product can be obtained.

A widely used catalyst for the manufacture of formaldehyde by oxidation of methanol is foraminous silver in the form of sintered mesh, gauze or crystals, particularly crystals prepared by electrolytic deposition from aqueous acid solutions of silver salts, such as silver nitrate. Such catalytic materials become sintered in the course of being heated to temperatures of from about 550 to about 700° C, to which they are normally exposed during adiabatic operation of the oxidation reaction.

Particularly in two-stage operations, it has been found preferable to employ finely divided silver crystals rather than silver gauze in the second oxidation stage in order to reduce methanol leakage to a satisfactory level while retaining satisfactory yields and conversion. The catalyst must, of course, give low methanol leakage throughout operation of the process. However, this is very difficult during the first several hours to several days of operation of the process. During this time methanol leakage is highest and is reduce to a relatively uniform lower volume at which it remains during the remainder of the life of the catalyst if operated at equivalent conditions. Thus, during the startup and first few days of operation, substantial quantities of formaldehyde may have to be relegated to less valuable applications because of high methanol content.

Silver crystals, particularly rather small crystals such as those which pass through a 20 mesh screen (U.S. Standard) or finer, are quite effective for the purpose of attaining quite low methanol leakage during startup. However, they suffer from the disadvantage that they tend to incur higher pressure drops within a shorter time than gauze and screen or coarse sized crystals which have higher void volumes. On the other hand, it has not proved practicable merely to substitute coarser silver catalysts for the reason that coarser catalysts, especially gauze and screens, are quite slow to reach sufficient levels of catalytic activity to avoid excessive methanol leakage during the startup and first few days of continuous operation of the process.

Thus, heretofore in order to avoid excessive pressure drop over the second catalyst bed and the expense and throughput limitations which result from high pressure drop, it was necessary to shut down the process frequently to replace the use catalyst with fresh catalyst.

BRIEF DESCRIPTION OF THE INVENTION

To overcome many of the disadvantages of the prior art processes of making formaldehyde from methanol using conventional silver catalysts, an improved two-stage process has been developed which incurs a less rapid rise in pressure drop over the critical second oxidation stage by employing as catalyst therein a composite fixed bed dual layer sintered catalyst prepared from an upstream layer of high void volume foraminous silver contiguous to a downstream layer of silver crystals having a lower void volume.

More particularly, the invention is directed to an improved process for the manufacture of formaldehyde by the silver-catalyzed oxidation of methanol in two stages in which is used as catalyst for the second oxidation stage a fixed composite catalyst prepared by sintering (a) an upstream layer of foraminous silver having a void volume of 75 to 90% and thickness ranging from about 10 to about 100 mm, the upstream layer being contiguous to (b) a downstream layer of crystalline silver particles having a void volume of 65 to 75% and which is at least about 5% below the void volume of the upper layer and thickness of form about 5 to about 20 mm.

DISCUSSION OF THE PRIOR ART

Composite catalysts have long been known in the manufacture of formaldehyde by oxidation of methanol over silver catalysts. For example, Japanese Patent Application 49-24889/1974 to Ishige et al. is directed to a dual layer silver catalyst having a downstream layer of 20–40 mesh crystals and an upstream layer of 40–90 mesh crystals. U.K. Pat. No. 1,375,319 discloses a somewhat similar dual layer silver catalyst having a downstream layer of 1 to 4 mm crystals and an upstream layer of 0.1 to 1 mm crystals. Similar dual layer catalysts are also disclosed in German Pat. Nos. 1,231,229, 1,294,360 and 1,903,197. Furthermore, German Pat. No. 2,322,757 to Aiche et al. discloses a multiple layer silver catalyst having layers of successively coarser size from the upstream side to the downstream side of the catalyst bed.

Quite contrary to the present invention, the prior art dual layer catalysts all appear for various reasons to have utilized the finer catalytic material in the upper (upstream) layer and the coarser material with higher void volume in the lower (downstream) layer of the composite structure. Furthermore, such prior art composite catalysts have never been disclosed to have any particular advantage in two-stage formaldehyde processes.

DETAILED DESCRIPTION OF THE INVENTION:

The overall sequences and conditions for operation of the process of the invention are similar to those disclosed in U.S. Pat. No. 2,462,413 and are preferably within the ranges taught by Northeimer in the above-referred allowed U.S. patent application. Thus, typically the process of the invention will be run within the following operating limits:

| Oxidation Stage | Mole Ratio Air to Methanol | Adiabatic Temp. (° C) | Space Velocity (hrs$^{-1}$) |
|---|---|---|---|
| 1st | 0.80 – 1.29 | 550 – 700 | 50,000 – 2,000,000 |
| 2nd | 1.70 – 2.40 | 550 – 700 | 50,000 – 3,000,000 |

Suitable catalytic materials for use in the process of the invention include foraminous silver metal in the form of sheets of gauze or screen and crystals, particularly electrolytic silver crystals as described hereinabove.

In the first oxidation stage, either gauze, screen or crystals can be used. Usually, it is preferred to use a relatively open (high void volume) catalyst in order to minimize pressure drop over the first stage. It will, of course, be apparent that methanol leakage is not a critical factor in the first oxidation stage since the effluent from the first oxidation stage is passed to a second stage. A preferred first stage catalyst is comprised of several layers of 20 mesh silver gauze made from 0.014 inch diameter silver wire. The catalyst bed of the first oxidation stage should be at least about 10 mm deep and preferably at least about 20 mm in thickness. On the other hand, the bed depth will not ordinarily be more than about 100 mm and usually no more than about 50 mm to avoid unnecessary pressure drop. A particularly suitable first stage catalyst is comprised of a stack of 40 sheets of 20 mesh silver gauze having a thickness of about 28 mm.

In the second oxidation stage, the process of the invention utilizes a composite sintered silver catalyst comprising an upstream layer prepared from foraminous silver having a void volume of from 75 to 90% prior to being sintered. The thickness of this upper layer should be from about 10 to 100 mm and preferably from about 20 to about 50 mm. Either gauze or screen or crystals of silver may be used as the catalytic material for the upstream layer of the catalyst. However, gauze and screen are preferred because of the more uniform nature of the voids therein. When gauze or screens are used for the upstream layer, the desired thickness of the layer is attained by stacking sheets of the material on top of each other to the required depth. When crystals are used, they will usually be placed on a suitably sized screen support which, in the usual downflow operation of the oxidation stage, bears upon the downstream layer of the composite catalyst.

Silver crystals must be used in the downstream layer of the composite catalyst in order to obtain low methanol leakage during the startup phase of operating the process. The void volume of the crystals must be within the range of 65 to 75% and be at least about 5% and preferably 10% lower than the void volume of the upper layer before sintering. In other words, if the void volume of the upper layer is 80%, the void volume of the lower layer must be no greater than 75%. It is preferred that the void volume of the lower layer be from 67 to 72%. The thickness of the lower layer should be at least 5 mm but no greater than about 20 mm. A thickness of from 8 to 15 mm is preferred.

It will be understood by those skilled in the art of silver catalysis that, at the temperatures encountered in the formaldehyde process (550°–700° C), both the gauze or screen and the crystals become sintered into a coherent porous mass having foramina extending throughout. It has been postulated that the more active form of the catalysts exists only after sintering. However, no special procedures are necessary to accomplish this other than the usual modes of startup and operation of the process, both of which are well understood by those skilled in the art. However, treatment of the surface of the catalytic materials prior to startup may be carried out to clean the surface of the metal or otherwise to render the surface more amenable to the formation of active catalytic sites thereon. Such pretreatments may raise the overall level of catalytic activity. Nevertheless, the same relative advantages of the above-described composite catalyst are obtained either with or without such surface pretreatment.

The advantages of the invention can be seen by reference to the following example:

EXAMPLE

A mixture of air, methanol vapor and steam in a weight ratio of 0.245 gram of air per gram of methanol and 0.053 grams of steam per gram of methanol is preheated to 118° C, passed through a primary converter containing 50 sheets (35 mm depth) of 20 mesh silver gauze, and thereafter cooled from the exit temperature of 600° C to 195° C by a water-cooled heat exchanger. The methanol feed rate through the primary converter is 5,350 kg/hr.m$^2$ which is equivalent to a space velocity of 544,000 reciprocal hours. The primary converter effluent gases are passed through a cartridge filter to prevent contamination of the secondary catalyst and mixed with additional 100° C filtered air in a ratio of .0216 gram of air per gram of initial methanol. This total mixture is then passed through a secondary converter containing a two-layer catalyst consisting of 40 sheets (28 mm depth) of 20 mesh silver gauze manufactured from 0.014 inch diameter fine silver wire resting atop 10 mm of 20 to 30 mesh size electrolytically prepared silver crystals. The total feed rate of 12,455 kg/hr.m$^2$ through the second stage catalyst is equivalent to a space velocity of 788,000 reciprocal hours. (As used herein, the term "space velocity" refers to the ratio of the volume of gas emerging from the catalyst per hour to the volume of catalyst.) The effluent gases are then promptly cooled from 640° C to 242° C by a water-cooled heat exchanger. The cooled gas is then passed through an absorber countercurrently to a stream o water where essentially all of the condensible portion of the second stage effluent gases is removed. The resulting liquid product is an aqueous 56% by weight formaldehyde solution containing less than 2% by weight methanol.

The above example is an improvement over the above-referred process taught by Northeimer in that the useful life of the secondary catalyst is considerably longer by virtue of the fact that it develops resistance to flow at a slower rate than the prior art secondary catalyst. In addition, this extended life can be obtained without suffering any significant change in the length of the startup period wherein the methanol leakage exceeds 2% by weight methanol in the formaldehyde product. By way of comparison, when the two-stage catalyst of the invention is replaced by a 19 mm depth bed of 20 to 30 mesh size silver crystals, as shown by Example I of the above-referred Northeimer patent application, the catalyst would have to be replaced after only 32 days because the pressure drop across the secondary converter would have reached 280 mm Hg, thus exceeding the capability of the air blowers to continue to provide air at the previous rate. On the other hand, the catalyst of the invention developes a pressure drop of only 205 mm Hg after 32 days and is able to continue to operate for 64 additional days before reaching a pressure drop of 280 mm Hg. In addition, the 19 mm single layer bed of 20 to 30 mesh silver crystals requires approximately 9 hours of operation after startup to reach a methanol concentration of 1.3% in the product. Similarly, the dual layer catalyst of the Example requires approximately 10 hours of operation after startup to reach a methanol concentration of 1.3% in the product. Thus, the catalyst of the invention is quite equivalent in its initial performance with regard to methanol leakage and far superior with regard to useful life as limited by allowable pressure drop.

We claim:

1. In a process for the manufacture of formaldehyde by the silver catalyzed oxidation of methanol in two series stages in which the second stage is typically operated with mole ratio of air to methanol of 1.70 -2.40, adiabatic temperature of 500°–700° C and space velocity of 50,000–3,000,000 $hr^{-1}$, the improvement comprising using as catalyst for the second oxidation stage a fixed composite catalyst prepared by sintering (a) an upstream layer of foraminous silver having a void volume of 75 to 90% and thickness of from about 10 to about 100 mm, the upstream layer being contiguous to (b) a downstream layer of crystalline silver particles having a void volume of 65 to 75%, which is at least about 5% below the void volume of the upper layer, and thickness ranging from about 5 to about 20 mm.

2. The process of claim 1 in which the foraminous silver of the upstream layer is in the form of crystalline silver particles.

3. The process of claim 1 in which the foraminous silver of the upstream layer is in the form of a plurality of overlying gauze or screen sheets.

4. The process of claim 3 in which the foraminous silver is 20 mesh screen.

5. The process of claim 1 which the upper layer is from about 20 to about 50 mm thick.

6. The process of claim 1 in which the void volume of the lower layer is from about 67 to 72%.

7. The process of claim 6 in which the crystalline silver particles of the downstream layer pass through a 20 mesh screen and are retained on a 30 mesh screen.

8. The process of claim 1 in which the lower layer is from about 8 to about 15 mm thick.

9. The process of claim 1 in which the void volume of the lower layer is at least 10% below the void volume of the upper layer.

* * * * *